United States Patent [19]

Blevins et al.

[11] Patent Number: 4,970,891

[45] Date of Patent: Nov. 20, 1990

[54] APPARATUS FOR MEASURING GASEOUS IMPURITY IN SOLIDS

[75] Inventors: Donald R. Blevins; Gottlieb C. Gaeke, Jr.; Doni G. Grande; Robert N. Sanders, all of Baton Rouge, La.

[73] Assignee: Ethyl Corporation, Richmond, Va.

[21] Appl. No.: 457,310

[22] Filed: Dec. 26, 1989

[51] Int. Cl.$^5$ ............................................. G01N 27/18
[52] U.S. Cl. ................................. 73/19.01; 73/25.03
[58] Field of Search ......................... 73/19, 27 R, 1 G

[56] References Cited

U.S. PATENT DOCUMENTS

| | | | |
|---|---|---|---|
| 3,150,516 | 9/1964 | Linnenbom et al. | 73/19 |
| 3,177,700 | 4/1965 | Sier | 73/19 |
| 3,427,863 | 2/1969 | Schultz | 73/19 X |
| 3,603,134 | 9/1971 | Norem | 73/27 R |
| 3,943,751 | 3/1976 | Akiyama et al. | 73/27 R |
| 4,112,737 | 9/1978 | Morgan | 73/19 X |
| 4,254,654 | 3/1981 | Clouser et al. | 73/27 R |
| 4,813,267 | 3/1989 | Norem et al. | 73/27 R X |

Primary Examiner—Hezron E. Williams
Assistant Examiner—Joseph W. Roskos
Attorney, Agent, or Firm—David E. LaRose

[57] ABSTRACT

The apparatus of this invention provides an improved thermal conductivity detector for determination of low levels of gaseous impurities vaporized from solid samples. In particular, a hydrogen impurity vaporized from solid polysilicon beads can be determined down to a detectable limit of about 0.1 ppm by weight. The improvement is comprised of a syringe injection pump for calibration of the instrument, a computer for controlling the syringe infusion pump and for calculating the analytical results, and means for controlling pressure and mass flows of the gas streams.

19 Claims, 2 Drawing Sheets

APPARATUS FOR MEASURING GASEOUS IMPURITY IN SOLIDS

FIELD

This invention relates to a convenient and reliable means for accurately determining the amount of gaseous impurity within a solid material.

REFERENCE TO MICROFICHE APPENDIX

Included in Appendix A is a microfiche listing of a computer program which can be used with the apparatus of this invention. The microfiche appendix contains a total of 221 frames.

BACKGROUND

Precise low level measurement of gaseous impurities in solid materials is an extremely difficult and time consuming task. By low level measurement is meant determination down to about 0.1 parts per million (ppm) by weight of gaseous impurity in the solid materials. In a commercial production unit, it is important to be able to obtain a precise and relatively quick determination of the amount of gaseous substance in solid materials in order to improve the purity of the final product.

One particularly important gaseous impurity determination is the measurement of hydrogen impurity in polysilicon solids such as beads, chunks, film, etc. High purity polysilicon beads are an important raw material in the production of semiconductor materials and devices.

Previously, it had taken up to 6 to 8 hours to determine the amount of hydrogen impurity in a sample of solid silicon. Constant operator attention was usually required during the analysis of the sample. Even with constant operator attention, the possibility of an error in analyzing the sample was great. Hence, a need existed for a reliable, less labor intensive way or detecting and determining low levels of hydrogen impurity in silicon.

SUMMARY OF THE INVENTION

In accordance with this invention, an apparatus has now been developed that can precisely determine the gaseous impurity in a solid sample down to a detectable limit of about 0.1 ppm by weight. The apparatus is comprised of means for automatically calibrating a thermal conductivity detector in addition to means for controlling system pressure and gas stream flows. With the apparatus of this invention, low levels of gaseous impurities within solids can be measured with a minimum of operator attention.

In a preferred embodiment of the invention, the improved thermal conductivity analyzer for determination of the amount of an impurity that is vaporized from a solid by a heater and introduced into a carrier gas stream, is comprised of (a) means for automatically injecting a calibration gas for calibrating the analyzer, and (b) means for automatically controlling pressure and mass flow of a sample gas in a first gas stream and for controlling mass flow of a reference gas in a second gas stream. In another preferred embodiment of the invention, the analyzer system is further comprised of a computer. The computer is used to monitor the temperature, pressure, and flows; to calibrate the system; and to calculate the analytical results.

The improvement of this invention overcomes the difficulties of accurately determining the amount of a gaseous impurity in a solid caused by the slow release of the gaseous impurity from the solid as the solid is heated. For example, it has been found that when polysilicon beads produced by the decomposition of silane are heated to about 1200° C., the release of hydrogen extends over a period of about 20 minutes to about 2 to 3 hours. While not wishing to be bound by theory, it is believed that the slow release of hydrogen from the polysilicon beads is due to the breaking of hydrogen bonds within the solid polysilicon as it is heated. Hydrogen is an undesirable impurity in polysilicon beads produced by the decomposition of silane, and heretofore, the slow release of this impurity from the polysilicon beads posed a number of difficulties.

Instruments known to be useful for gas measurements can accurately measure gaseous impurities only if the impurities are released quickly from the solids. When using a gas chromatograph, peaks normally last from several seconds up to several minutes for each gaseous component detected. However, hydrogen is released much too slowly from solid polysilicon particles to be measured by standard gas measurement devices including standard chromatographs and gas analyzers.

A feature of this invention is that it enables accurate and automatic determination of the amount of gas vaporized from a solid even when the gas is released from the solid over a period ranging from about 20 minutes up to six hours or more. Another feature of this invention is that such analysis can be performed with a minimum of operator attention. Other features of the invention will become evident from the ensuing description.

THE DRAWINGS

A schematic diagram of a typical, but preferred, arrangement of the components of this invention is illustrated in FIG. 1.

FIG. 2 is an illustration of a typical device for holding the solid sample to be analyzed for a gaseous impurity.

DETAILED DESCRIPTION

Figure 1:
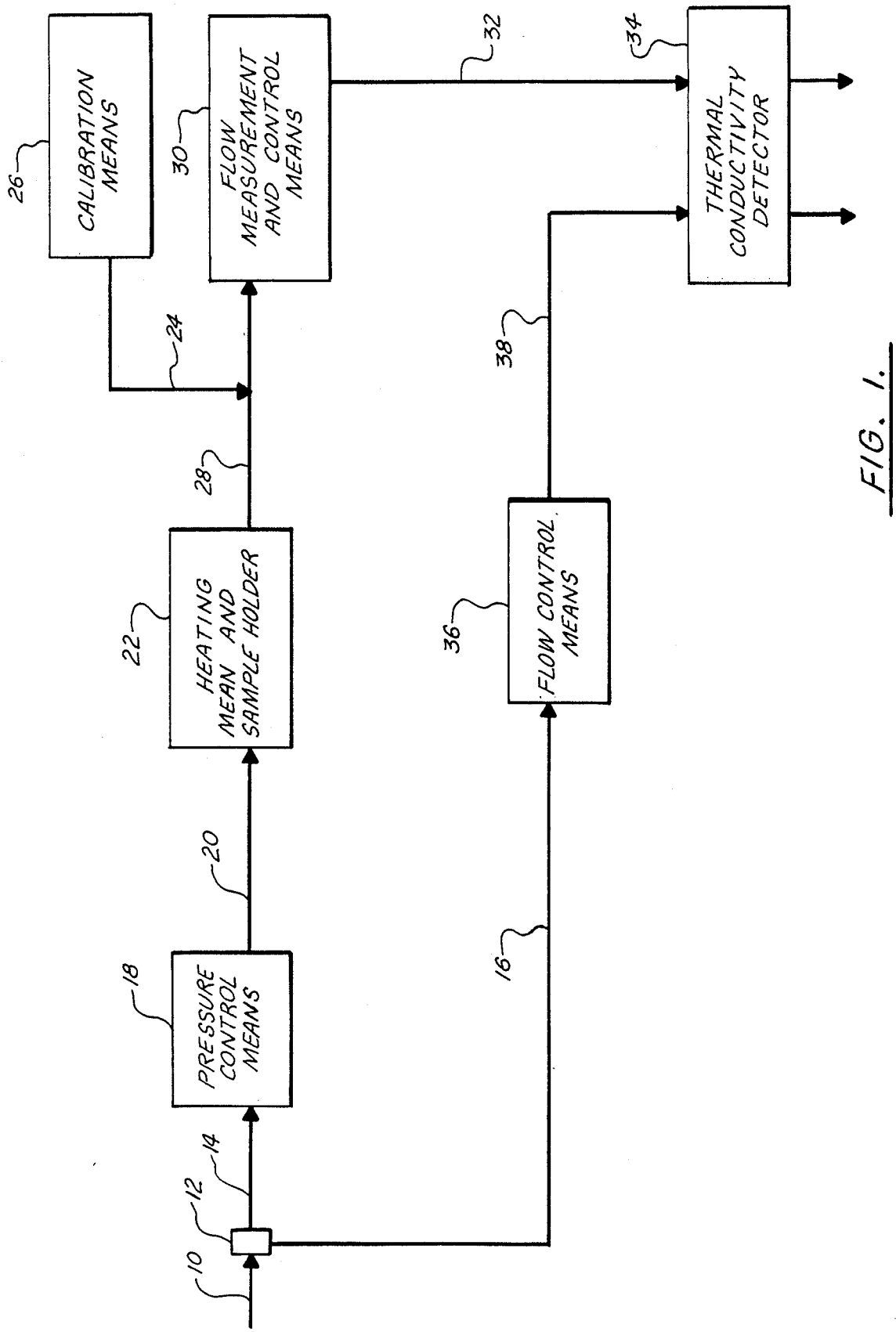

In the form depicted in FIG. 1, there is provided an apparatus for determination of a gaseous impurity in a solid sample down to a detectable limit of about 0.1 by weight which comprises (a) means for introducing a carrier gas, (b) means for splitting the carrier gas into a first stream and a second stream, (c) means for vaporizing an impurity in a solid sample such that the impurity is introduced into the first stream, (d) means for detecting the vaporized impurity in the first stream, (e) means for automatically calibrating the detection means, (f) means for controlling pressure and mass flow of the first stream, and (g) means for controlling mass flow of the second stream.

Referring now to FIG. 1, the apparatus in the form depicted includes pressure controller 18, heater 22, calibration means 26, first stream flow controller 30, second stream flow controller 36, and thermal conductivity detector 34. Line 10 transmits a continuous flow of a carrier gas into the apparatus and tee 12 splits the carrier gas into a first stream 14 and a second stream 16. Pressure controller 18, measures and adjusts the pressure in line 14 and transmits the resultant carrier gas stream to the the heater 22 through line 20. The sample to be analyzed is placed in the heater, preferably in a sample holder similar to the device 40 illustrated in FIG. 2 such that the carrier gas stream 20 can flow through the sample holder as both the holder and sample are heated. Upon heating the sample, impurities from the solid are released into sample stream 28, which then contains the vaporized impurity and the carrier gas stream. During calibration, the heater is not used. Instead, calibration means 26 injects a predetermined amount of calibration gas at a predetermined rate into sample stream 28 such that sample stream 28 contains the calibration gas and the carrier gas rather than the carrier gas and the vaporized impurity. First flow controller 30 receives, measures and controls the flow of the sample gas stream and transmits the resultant sample stream to thermal conductivity detector 34 via line 32. Preferably sample stream 28 is cooled to about room temperature prior to entering first flow controller 30. Cooling may be done by any means well known in the art, including using a length of coiled tubing to carry the sample stream from the heater to the flow controller. Second flow controller 36 receives and controls the flow of the second gas stream 16 and transmits the resultant stream which serves as a reference gas, to the thermal conductivity detector 34 via line 38. As those skilled in the art well know, the thermal conductivity detector senses the difference in thermal conductivity of the sample gas stream as compared to the reference gas stream as the amount of vaporized impurity in the sample gas stream varies.

Figure 2:
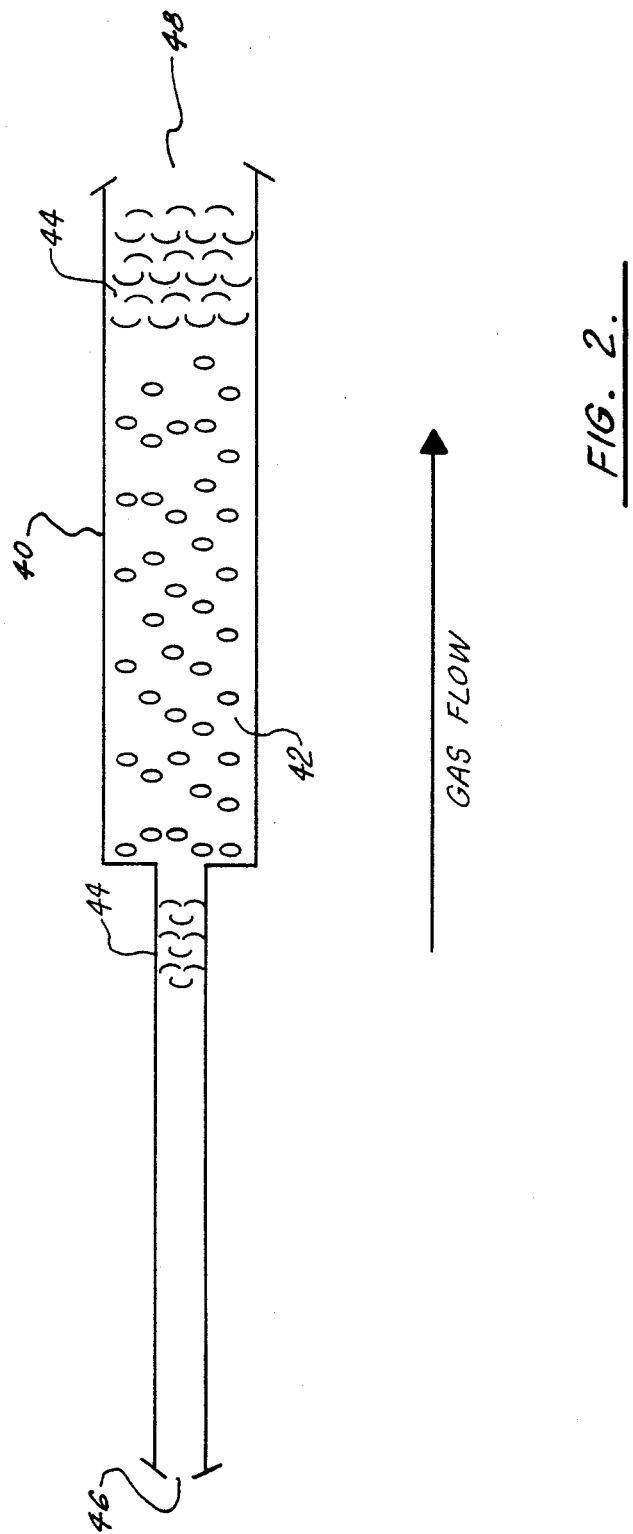

Illustrated in FIG. 2 is a typical device 40 for holding a solid sample that is to be analyzed for its impurity by the apparatus depicted in FIG. 1. The sample holder includes an inlet 46, an outlet 48, and means 44 for retaining the solid sample 42 within the sample holder 40. After being placed in the heater 22, inlet 46 is connected to carrier gas stream 20, and outlet 48 is connected to sample gas stream 28. In a preferred embodiment, the inlet 46 is smaller than the outlet 48. This difference in the size of the inlet and outlet of the sample holder is to minimize a pressure surge as the sample within the holder is heated. Those skilled in the art can readily determine the size of the inlet and outlet of the sample holder required to prevent an undue pressure while the sample is being heated.

In accordance with this invention, it has now been discovered that greater precision in determining the amount of impurity in a solid sample can be achieved by utilizing means for automatically calibrating the apparatus. The means for automatically calibrating the apparatus may include any means known in the art for automatically and accurately injecting a calibration gas 24 into sample stream 28. Such an automatic injection device may consist of a solenoid valve and timer for allowing calibration gas at a given pressure for a set period of time to enter the apparatus, or use of a volumetric flow pump, or any similar device for controlling the amount of calibration gas injected into to first gas stream. In a preferred embodiment of the invention, a syringe infusion pump is utilized. This syringe infusion pump can be connected to a timer, or interfaced with a computer for controlling the injection of a calibration gas. In another preferred embodiment, the means for calibrating is connected to a computer that is programmed to control the timing and hence quantity of calibration gas being injected. By using the syringe infusion pump coupled to a computer, one can readily simulate the slow release of a hydrogen impurity from a solid polysilicon sample as well as the release of other gases from other solids.

As depicted in FIG. 1, there are means for controlling the pressure and mass flow of gases in the first stream (carrier gas stream) and means for controlling the mass flow in the second stream (reference gas stream). Preferably, the pressure control device is situated such that the pressure of the carrier gas stream is adjusted before the carrier gas enters the heater. In another preferred embodiment of the invention, the mass flow of the sample gas stream is adjusted after the sample gas exits the heater and before the sample gas enters the thermal conductivity detector. Standard independent controllers can be used for controlling pressure and mass flows or analog outputs from these controllers can be interfaced with a computer. In addition to controlling the rate of injection of the calibration gas, and monitoring of pressures and flows in the first and second gas streams, the computer can also be used to calculate the quantity of gaseous impurity in the sample being analyzed. In accordance with the preferred embodiment of this invention, a computer is used to control the heating of the sample, the monitoring of the pressure of the sample gas stream and mass flows of the sample and reference gas streams, and the calculation of results based on the thermal conductivity measurements of the reference gas and sample gas streams. By utilizing a computer to control the calibration of the apparatus, and analysis the data collected, accurate and reliable measurements down to a detectable limit of about 0.1 ppm by weight have been achieved. In addition, only about 15 minutes of operator time are required to analyze a given sample of solid for its gaseous impurity.

The device as described herein has been used to measure such gases as hydrogen in polysilicon beads. The apparatus can be adapted to measure hydrogen in solid polysilicon from about 0.1 parts per million by weight to greater than 40 parts per million by weight. The apparatus can also be used to measure the amount of other gaseous impurities which can be vaporized by heating solid silicon, as well as the amount of other gaseous impurities vaporized from other solid materials. The apparatus of this invention has proven to be useful in measuring the amount of gaseous impurity when those impurities are released slowly from solid materials, however, the device may also be used to measure gaseous impurities that are released at a faster rate than the release of hydrogen from solid silicon particles. By calibrating the apparatus with the same gaseous impurity that is vaporized from the solid sample to be analyzed, and by programming the injection rate for calibration of the thermal conductivity detector, the apparatus of this invention can easily be adapted to the measure a variety of gaseous impurities vaporized from a variety of solid samples.

When calibrated with the gaseous impurity to be measured, the apparatus of this invention yields precise measurement of the gaseous impurity vaporized from solid sample thus analyzed. Analytical results utilizing the apparatus of this invention have a standard deviation of about 0.1 parts per million by weight.

Average cycle time for analysis of a sample of polysilicon beads for a hydrogen impurity is in a range of about 3 to about 4 hours. This cycle time is considerably less than the cycle time required with previous methods of analysis. Accordingly, this invention is not limited to a cycle time of about 3 to about 4 hours as more or less time may be required depending on the sample to be analyzed, the gaseous impurity present in the solid, and the release rate of the impurity from the solid sample.

When analyzing a solid sample, there is means for vaporizing the impurity in the solid sample. The means is typically an electric oven. However, any heating means known in the art may be used to effect release of the impurity from the solid sample. Preferably the oven is thermostatically controlled, and most preferably, the oven temperature is computer controlled such that the temperature is increased at a predetermined rate to heat the sample and decreased as rapidly as possible at the end of the analysis cycle.

Once released from the solid by heating, the gaseous impurity is introduced into the carrier gas stream and thence into means for detecting the gaseous impurity. By use of a suitable device for holding the sample to be heated, the vaporized impurity is introduced into the carrier gas stream and loss of carrier gas containing the vaporized impurity is minimized. In this regard, the solid sample to be analyzed can be placed in any device known in the art such that it can be heated to the desired temperature and such that the gaseous impurity released from the solid is introduced into the carrier gas stream as the carrier gas stream passes through the device holding the solid sample. A typical sample holding device may be a box, tube, or any such similar device for holding a solid sample. Preferably, the sample holding device contains two openings, an inlet and an outlet for passage of the carrier gas over the heated sample contained within the sample holding device. When analyzing solid silicon to determine the amount of hydrogen impurity therein, the sample is heated to about 1200° C. from bout 225° C. in about 45 minutes or less. Therefore, the sample holding device used should preferably withstand temperatures in the range of about 1200° to about 2000° C. Hence the sample holding device can be made of metal, ceramic, quartz or the like. When analyzing polysilicon for a hydrogen impurity, a quartz tube is the most desirable device for holding the solid sample.

There must also be means for retaining the sample to be analyzed within the quartz sample tube as the sample tube is handled and as the carrier gas flows through the sample tube. Again the materials used for retaining the sample within the sample tube preferably should be able to withstand temperatures in the range of about 1200° to about 2000° C. One such material found useful for holding the sample within the sample tube is comprised of a quartz wool packing. Once the solid sample is placed in the sample tube, the quartz wool packing is used to prevent the solids from falling out of the tube when the tube is handled or placed in position for analysis. Other materials known in the art may also be used to retain the solid sample to be analyzed within the sample tube.

When utilizing a quartz tube for holding the sample to be analyzed, the tube is usually designed for easy connection to the carrier gas inlet and sample gas outlet streams. Hence, each end of the sample tube may contain a flange, or clamping device which can be connected to the carrier gas stream to provide an airtight connection. In a particularly preferred embodiment of the invention, the sample tube inlet and outlet each contain male standard taper fittings which can be fitted to female fittings on the carrier gas inlet stream 20, and sample gas outlet stream 28 as illustrated in FIGS. 1 and 2. Other solid materials can also be analyzed using the quartz sample tube containing the standard taper fittings. Hence, solids such as powders, film, and chunks, as well as beads, may be placed in the quartz sample tube and held in place using the quartz wool packing.

Accordingly, when the sample holding device contains standard taper fittings, it is desirable to maintain a relatively low pressure within the sample gas line, in order to minimize the chance of damage to the equipment or loss of the sample gas to be analyzed. The apparatus of this invention can be used with pressures in the range of about 760 mm Hg absolute to 1000 mm Hg absolute or higher. Normally, the inlet carrier gas pressure is about 25 pounds per square inch gauge. Hence, means for controlling the pressure of the carrier gas stream 14 is utilized to adjust the carrier gas pressure to a range of about 760 mm Hg to about 900 mm Hg and most preferably to about 800 mm Hg.

Components which may be used to construct the apparatus of this invention include many standardly available devices. As an example, typical components used in the sample gas stream included, a model 600A Barocell pressure sensor, a Datametrics model 72W606-20-000 pressure controller, and a Datametrics model 71W890-09-302 servo valve. The furnace used to heat the solid sample was a Lindberg model 55035 muffle furnace modified so that the temperature is controlled by an Omega Engineering model CN-2011-K-D2 temperature controller. Mass flow measurement and control devices used in the sample and reference gas streams were Datametrics model 71W824-73-312 flow control valves operated by a Datametrics model 7W82721000 five channel flow controller. For measurement of thermal conductivity, a Gow-Mac model 40-250/252 thermal conductivity detector was used. Injection of the calibration gas was accomplished by using a Harvard Apparatus model 22 syringe infusion pump. Analog inputs from the pressure sensing and mass flow measurement devices as well as thermal conductivity from the thermal conductivity detector were fed into a IBM-PC AT personal computer having 640 kilobytes RAM, two 5.25 inch floppy disk drives, one parallel port connected to an Epson printer, and a VGA display adapter and monitor. Those skilled in the art can readily assemble comparable components suitable for analysis of solid samples utilizing the apparatus of this invention.

Several interfaces in the computer controlled various aspects of the apparatus. Two types of controlling interfaces were used. The first was a Data Translation DT2801 General Purpose input/output (I/O) interface having analog and digital input and output lines. Digital outputs from the computer were used to open and close solenoid valves on vent and bypass lines as well as a solenoid valve for nitrogen cooling of the sample once the analysis was complete. Analog outputs from the pressure and flow sensors and the thermal conductivity detector were fed into the computer. The second type of controlling interfaces were serial interfaces. These were configured as COM1 and COM 2 on the personal computer. COM1 was used to control and monitor the furnace temperature via the Omega temperature controller. COM2 was used to control the Harvard Apparatus syringe infusion pump.

One typical computer program used to manage the operation of the apparatus and calculate the results of the analysis is listed in the microfiche appendix. This computer program was written in the language Asyst (Asyst Software Technologies, Inc. 100 Corporate Woods, Rochester, N.Y., 14623. This invention is not limited, however, to use of the computer program contained in the appendix as those skilled in the art can readily assemble a computer program which can be used to control the apparatus and calculate the analytical results. Accordingly, the apparatus of this invention is not limited by the use of any particular computer program.

Although other computer programs may be utilized with the apparatus of this invention, the program listed in the microfiche appendix has been found to be the most desirable for accurate determination of low levels of hydrogen in solid polysilicon. The computer program is menu driven and includes a number of features to aid the operator in performing the analysis with a minimum of operator attention. Within the computer program is the autocalibration sequence. When determining the amount of hydrogen impurity in solid silicon, pure hydrogen is used as a standard calibration gas. Known amounts of hydrogen are injected using computer control of the syringe pump to simulate the hydrogen peak profile seen during a normal sample run. The computer keeps track of ten injections at each of four standard concentrations. If a new injection is outside the region of reasonable statistical variation, that run is rejected. Once there are ten runs stored for any calibration volume, subsequent runs will replace the oldest runs. A quadratic calibration curve is constructed using the data from the calibration runs. The computer also keeps track of the time between calibration runs. The maximum time between calibrations is thirty days, at which time a computer message will indicate that it is time to recalibrate the apparatus.

Once calibration of the instrument is performed, a solid sample of polysilicon can be analyzed. In a typical run, 50 to 55 grams of polysilicon beads are placed in the quartz sample tube. The sample tube used is one that has been used previously or one that has been dried by heating to about 1200° C. Quartz wool used to hold the solid sample within the tube is also dried at a temperature of about 1200° C. before use. The quartz wool is packed tightly against the solid silicon beads so that the beads can not move when the tube is placed in a horizontal position. Silicon stopcock grease is used on the taper fittings of the sample tube, and springs are used to ensure a tight fit of the female taper fittings with the male taper fittings at each end of the sample tube. Start of the sample run is then selected from the computer generated menu and the weight of the sample to be analyzed is entered. Analysis of the sample continues until the computer determines that the end of the run has been reached. Several different parameters are used to indicate the end of the sample run. One such parameter is the maximum collection time. Another parameter is the change in signal level of the thermal conductivity detector over a period of time. If the change is less than a preset value, the run is terminated.

The initial heat up sequence selected for analysis of polysilicon beads includes heating the sample to about 225° C. for a period of time to drive off any surface-absorbed gases prior to increasing the temperature to about 1200° C. for analysis of hydrogen in the sample.

Once the run is started, the flow of carrier gas and sample gas is adjusted by means for controlling mass flow. The means for controlling mass flow are Datametrics model 71W82721000 flow controllers. In a typical run wherein hydrogen is released from silicon beads, the mass flow of the carrier gas and reference gas streams is adjusted to about 10-mL per minute by setting the Datametrics mass flow controller to about 0.45 on the digital display.

Other components of the invention are controlled by the computer. One such component is an automatic valve for blowing nitrogen over the sample tube once the run is complete in order to cool the tube so that it can be removed from the oven. Other components are an automatic vent valve and bypass valve provided in the sample lines to prevent an inadvertent high pressure from damaging the equipment. This automatic vent-valve is also controlled by the computer on the basis of the analog input from the pressure sensing device.

When analyzing a solid sample for its gaseous impurity content, a carrier gas is selected such that the difference in thermal conductivity between the sample gas stream and the reference gas stream is maximized. Carrier gasses which may be used with this invention include argon, carbon dioxide, helium and nitrogen. When analyzing polysilicon for its hydrogen impurity content, argon is preferably chosen as the carrier gas.

It will be recognized and appreciated that the apparatus of this invention is susceptible to considerable variation within the spirit and scope of the invention and appended claims.

We claim:

1. In a gas analyzer apparatus, which uses a thermal conductivity detector for determination of the amount of an impurity that is vaporized from a solid by a heater and introduced into a carrier gas stream such that the amount of gaseous impurity vaporized from the solid is determined by difference in thermal conductivity in a first gas stream as compared to the reference gas in a second gas stream, the improvement which comprises (a) means for automatically injecting a calibration gas for calibration of the apparatus, and (b) means for automatically controlling pressure and mass flow of a sample gas in the first gas stream and for controlling mass flow of a reference gas in the second gas stream.

2. The improvement of claim 1 wherein the means for automatically controlling mass flow of the sample gas stream is situated such that the mass flow of the sample gas is adjusted after the sample gas exits the heater and before the sample gas enters the thermal conductivity detector.

3. The improvement of claim 1 wherein the means for automatically injecting a calibration gas is a syringe infusion pump.

4. The improvement of claim 3 further comprising a computer for automatic control of the syringe infusion pump.

5. The improvement of claim 1 wherein the means for automatically controlling pressure of the carrier gas stream is situated such that the pressure of the carrier gas is adjusted before the carrier gas enters the heater.

6. An apparatus for determination of a gaseous impurity in a solid sample down to a detectable limit of about 0.1 ppm by weight which comprises (a) means for introducing a carrier gas, (b) means for splitting the carrier gas into a first stream and a second stream, (c) means for vaporizing an impurity in a solid sample such that the impurity is introduced into the first stream, (d) means for detecting the vaporized impurity in the first stream, (e) means for automatically calibrating the detection means, (f) means for controlling pressure and mass flow of the first stream, and (g) means for controlling mass flow of the second stream.

7. The apparatus of claim 6 wherein the means for controlling mass flow of the first stream is situated such that the mass flow of the first stream is adjusted after the first stream exits the means for vaporizing an impurity in the solid.

8. The apparatus of claim 6 wherein the means for automatically calibrating the detection means is a syringe infusion pump.

9. The apparatus of claim 8 further comprising a computer for automatic control of the syringe infusion pump.

10. The apparatus of claim 6 wherein the means for detecting the vaporized impurity in the first stream is a thermal conductivity detector.

11. The apparatus of claim 6 wherein the means for controlling pressure of the first stream is situated such that the pressure of the first stream is adjusted before the first stream enters the means for vaporizing an impurity in the solid.

12. An apparatus for determination of a hydrogen impurity in a solid silicon sample down to a detectable limit of about 0.1 ppm by weight which comprises (a) means for introducing a carrier gas, (b) means for splitting the carrier gas into a first stream and a second stream, (c) means for vaporizing a hydrogen impurity in a solid silicon sample such that the hydrogen impurity is introduced into the first stream, (d) means for detecting the vaporized hydrogen impurity in the first stream, (e) a syringe infusion pump for automatically calibrating the detection means, (f) means for controlling pressure and mass flow of the first stream, and (g) means for controlling mass flow of the second stream.

13. The apparatus of claim 12 wherein the means for controlling mass flow of the first stream is situated such that the mass flow of the first stream is adjusted after the first stream exits the means for vaporizing an impurity in the solid.

14. The apparatus of claim 12 further comprising a computer for automatic control of the syringe infusion pump.

15. The apparatus of claim 12 wherein the means for detecting the vaporized hydrogen impurity in the first stream is a thermal conductivity detector.

16. The apparatus of claim 12 wherein the means for controlling pressure of the first stream is situated such that the pressure of the first stream is adjusted before the first stream enters the means for vaporizing an impurity in the solid.

17. An apparatus for determination of a hydrogen impurity in a solid silicon sample down to a detectable limit of about 0.1 ppm by weight which comprises (a) means for introducing a carrier gas, (b) means for splitting the carrier gas into a first stream and a second stream, (c) means for vaporizing a hydrogen impurity in a solid silicon sample such that the hydrogen impurity is introduced into the first stream, (d) means for detecting the vaporized hydrogen impurity in the first stream, (e) a syringe infusion pump for automatically calibrating the detection means, (f) means for controlling mass flow of the first stream such that mass flow of the first stream is adjusted after the first stream exits the means for vaporizing an impurity in the solid, (g) means for controlling mass flow of the second stream, and (h) means for controlling pressure of the first stream such that the pressure of the first stream is adjusted before the first stream enters the means for vaporizing an impurity in the solid.

18. The apparatus of claim 17 further comprising a computer for automatic control of the syringe infusion pump.

19. The apparatus of claim 17 wherein the means for detecting the vaporized hydrogen impurity in the first stream is a thermal conductivity detector.

* * * * *